United States Patent [19]

Weiss

[11] Patent Number: 4,473,370
[45] Date of Patent: Sep. 25, 1984

[54] PROTECTIVE EYE SHIELD

[76] Inventor: Jeffrey N. Weiss, 77 Pond Ave., #C1003, Brookline, Mass. 02146

[21] Appl. No.: 301,517

[22] Filed: Sep. 14, 1981

[51] Int. Cl.³ .......................... A61H 1/02; A61F 13/12
[52] U.S. Cl. .................................. 604/402; 128/25 A; 128/163; 128/155
[58] Field of Search ................ 128/645, 76.5, 97, 114, 128/163, 260, 214 D, 249, 283; 2/15; 604/380, 399, 402

[56]  References Cited

U.S. PATENT DOCUMENTS

| | | | |
|---|---|---|---|
| 1,964,655 | 6/1934 | Williamson | 128/380 |
| 2,101,628 | 12/1937 | Padelford | 128/380 |
| 2,595,934 | 5/1952 | Ginsburg | 128/283 |
| 2,796,903 | 6/1957 | Gazelle | 128/402 |
| 3,054,400 | 9/1962 | Lizio | 128/163 |
| 3,149,943 | 9/1964 | Amador | 128/402 |
| 3,195,539 | 7/1965 | Hyman | 128/380 |
| 3,664,340 | 5/1972 | Morgan | 128/249 |
| 3,760,984 | 9/1973 | Theeuwes | 128/260 |
| 3,768,485 | 10/1973 | Linick | 128/402 |
| 4,127,127 | 11/1978 | Wong et al. | 128/260 |
| 4,193,401 | 3/1980 | Marinello | 128/163 |
| 4,232,671 | 11/1980 | Crump | 128/249 |
| 4,243,041 | 1/1981 | Paul | 128/402 |

Primary Examiner—C. Fred Rosenbaum
Assistant Examiner—Sherri E. Vinyard
Attorney, Agent, or Firm—Wolf, Greenfield & Sacks

[57]  ABSTRACT

A protective shield for patients whose eyelids are unable to protect and moisten the eye. The shield comprises a transparent plastic bag filled with transparent fluid lying over the patient's eye and supported by the surrounding orbital structure. The shield is secured to the head by an overlying circular soft rubber mask allowing visibility and magnification of the eye. The mask in turn is attached to the patient by a strap with a Velcro-type closure.

9 Claims, 4 Drawing Figures

PROTECTIVE EYE SHIELD

BACKGROUND OF THE INVENTION

In cases of severe injuries to the face resulting from chemical, electrical or combustion burns, accidents, surgery, etc., eyelid injury often impairs the lid's ability to protect and moisten the eye. Without this vital function, the eye will dry, and this may lead to severe infection resulting in blindness and possible removal of the eye.

Presently used techniques to protect the eye include the application of drops or ointments to the eye every thirty to sixty minutes, 24 hours a day, to keep it moist and prevent drying. There are multiple problems associated with this technique. As these patients tend to be severely injured, principle attention is directed to save the patient's life. Unfortunately, it is only when the patient's life is no longer threatened that the fact that the eye is drying out is noticed. Additionally, the nursing responsibilities or any other emergency may preclude the application of the medication into the eye according to the prescribed round-the-clock schedule. In accordance with another technique frequently used, a piece of thin plastic wrap or x-ray film is cut to size to cover the eye and is affixed to the skin surrounding the eye. Ointment is placed on the periphery of the wrap or film. If the ointment is not correctly applied or not frequently monitored, the eye will again dry out. In accordance with yet other techniques, if sufficient lid tissue is present, the eyelids may either be taped closed or the upper and lower eye lids may be sewn together. Disadvantages of taping the eye closed include (1) contamination of wounds by the adhesive tape; (2) inability of the tape to maintain lid closure; and (3) inability to examine the eye. Disadvantages of sewing the eye closed include (1) inherent risks of a surgical procedure in a seriously injured patient; (2) breakage of suture material; (3) pressure necrosis of the skin and/or infection at the operative site; (4) inadequate amount of tissue may be available secondary to the initial trauma; and (5) inability to examine the eye.

It is to the elimination of these problems that the present invention is directed whereby the eye is protected and the moisture of the eye maintained in the absence of adequate lid or tear amount and function.

OBJECT AND SUMMARY OF THE INVENTION

One important object of this invention to provide an improved technique for the maintenance of moisture and the protection of an eye whose eyelid function has been impaired.

It is another object of this invention to provide a disposable, inexpensive shield which is transparent and which, by its configuration and method of attachment, provides a clear magnified view of the eye for the doctor or nurse to examine, without removal of the device.

It is still another object of this invention to provide a device which not only shields the eye but, in addition, directly introduces antibiotics or other medicament to the eye.

To accomplish these and other objects, the protective eye shield of this invention is pillow-like in shape and comprises a sealed bag made of polyethylene film or other similar material which measures approximately 8 by 12 centimeters. The bag when filled with liquid has a thickness of approximately 1½ centimeters when placed on a flat surface. The film is heat sealed about the sides and is filled with a clear liquid such as sterile water. The water may or may not include a medicament solution. The bag which defines the shield is sized to sit on the orbital structure that surrounds the eye to be protected. The shield does not touch the cornea.

A mask made of rubber or some similar material and having an eye opening retains the shield in place by engaging the periphery of the bag and holding it against the orbital structure of the face. The mask in turn is held in place by a band attached to it that has a soft lining and a Velcro-type closure.

BRIEF FIGURE DESCRIPTION

DETAILED DESCRIPTION OF THE DRAWINGS

Figure 1:
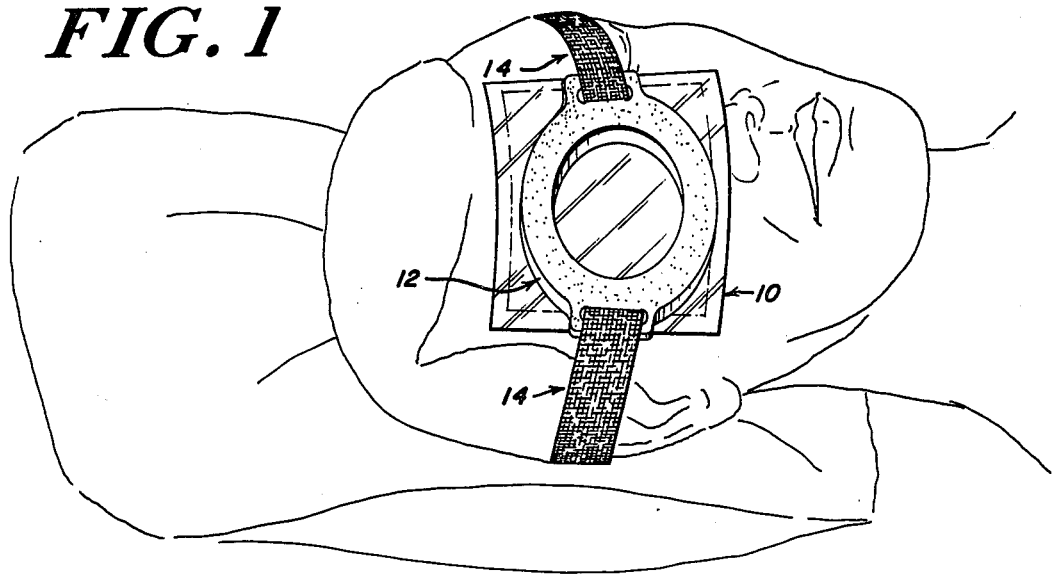
FIG. 1 is a pictorial illustration of the shield, mask and band of this invention in place on the head of a patient.
Figure 2:
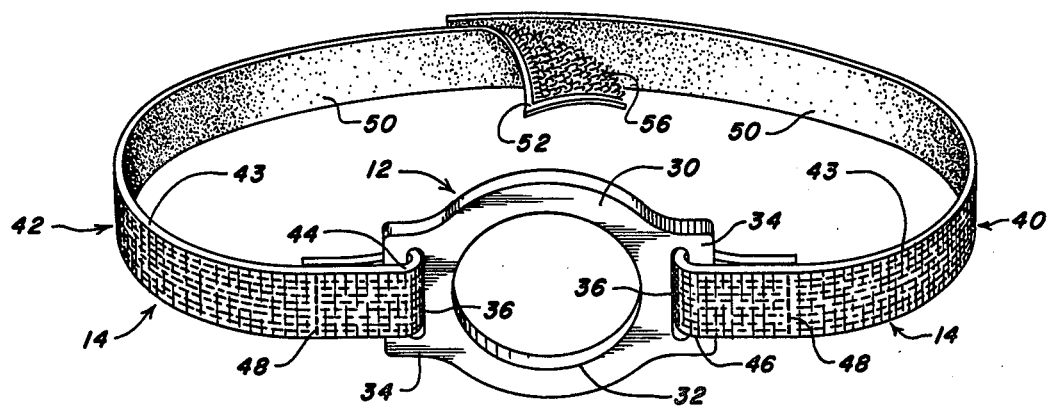
FIG. 2 is a perspective view of the shield, mask and strap removed from the patient and showing the strap closure.
Figure 3:
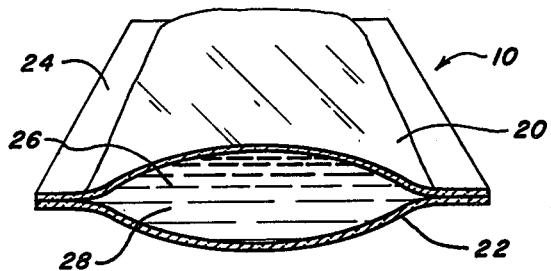
FIG. 3 is a cut away perspective view of the shield.

The embodiment of this invention shown in FIGS. 1–3 includes a shield 10, a mask 12 and strap 14. The shield 10 is made of upper and lower sheets of plastic film 20 and 22 heat-sealed together about their periphery as suggested at 24 to form a closed compartment 26. The upper and lower sheets may of course be formed from a single folded sheet necessitating heat sealing about only three sides. The thin sheets 20 and 22 typically may be made of a one mil transparent polyethylene film or some other material having high optical qualities, and substantial strength. While polyethlene is suggested for the material because of its flexibility, strength, transparency, etc., other materials may be used. It is essential, however, that the material be non-irritating to the skin and otherwise be non toxic in nature. The sheets 20 and 22 may be approximately 8 centimeters by 12 centimeters.

Compartment 26 is filled with a clear transparent liquid having high optical qualities such as sterile water 28. The liquid filled shield is highly pliable and its surfaces very soft. Therefore, it will conform readily to the contours of the orbital bone structure that surrounds the eye and when placed in position as shown in FIG. 1, its weight is evenly distributed on the bone structure so as to provide minimum discomfort. The shield does not touch the cornea. The filled shield 10 when placed on a flat surface has a thickness of approximately 1½ centimeters. It contains approximately 60–100 cc of liquid.

The mask 12 is in the form of a ring 30 which may be made of rubber or other pliable material and has a central opening 32 which is somewhat smaller than the plan area of the shield 10 so that when the mask is placed over the shield it overlies the periphery of the shield so as to hold it in place. This arrangement is shown in FIG. 1. The mask is provided with oppositely extending tabs 34 which are slotted as shown at 36 to receive the ends of a strap 14 to hold the mask in place over the shield on the orbital facial structure.

Strap 14 may take many different forms. In the embodiment shown, the strap is made of two parts 40 and 42 which may have a base fabric of elasticized webbing 43 stretchable in a longitudinal direction. End 44 of section 42 and end 46 of section 40 are threaded through slots 36 in the flanges 34 of the mask and may be permanently sewn in place. This is suggested by the seams 48 in FIG. 2.

The back of the strap 14 which is intended to lie against the surface of the skin preferably is lined with a soft, cotton, looped material which serves as the looped part of a Velcro-type fastener for closing the strap about the head. The soft looped cotton liner of course is stretchable with webbing 43 and is suggested at 50 in the drawings. The outer surface 52 of strap section 42 at its end 52 carries a Velcro patch 56 that has the hook like fasteners on it which are adapted to engage the loops of cotton liner 50 so as to close the band 14 about the head.

When the shield 10 is placed over the eye in the manner suggested in FIG. 1, it forms an air tight seal over the eye. The seal over the eye will cause any moisture from the body or air in the atmosphere trapped under the shield to condense so as to supply the necessary moisture to the eye and prevent it from drying. It will also be appreciated that when the shield is held in place by the mask 12, a natural curvature is imposed on the shield which causes the liquid to magnify the eye when viewed through the shield. The opening 32 in the shield allows the physician or nurse to examine the eye with the aid of the magnification, without removing the mask or shield.

Figure 4:
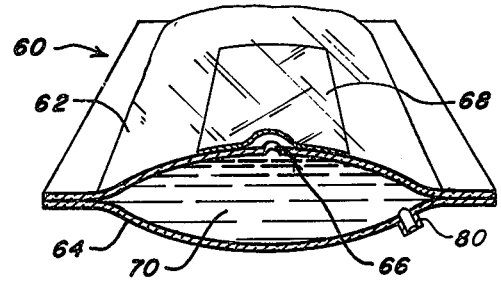
FIG. 4 is a view similar to FIG. 3 and showing another embodiment of shield oriented with the side normally overlying the eye on top.

In FIG. 4, another embodiment of shield is shown. Shield 60 of this embodiment differs from the embodiment of FIGS. 2 and 3 in that means are incorporated into the shield for enabling the liquid in the shield to diffuse through its wall at a controlled rate in order to medicate the eye. In accordance with this embodiment, shield 60 is composed of two sheets of film 62 and 64 similar to the sheets 20 and 22 of the first described embodiment. Sheet 62 which is intended to lie against the skin and face the eye is provided with a small opening 66 which is covered by a membrane 68 made of hydrogel or some similar material that has high permeability to water that allows the liquid 70 in the shield to diffuse slowly through it so that it may flow to the surface of the eye. The liquid 70 may typically contain an antibiotic or other medicament in solution so as to medicate the eye. Obviously the membrane 68 will be selected so as to provide a diffusion rate that is suitable for the particular medicament and eye condition presented. It will be appreciated that the shield 60 will be held in place by the mask 12 and strap 14 in the same manner as described above in connection with the shield 10.

In FIG. 4 the shield is shown to include a filler nipple 80 with a resealable membrane which allows a nurse, physician or other attendant to either add medicament to the liquid already in the shield or to introduce all the liquid and medicament into it. It is contemplated that the shield could be supplied by the manufacturer either filled with the liquid and with or without the medicament or empty, and the presence of a filler self sealing nipple will enable the user with the aid of a needle to introduce whatever is required. Such a device may be provided in any of the embodiments of the invention, and should be so located on the shield so that it does not lie against the skin or interfere with the application of the mask.

Having described the invention in detail, those skilled in the art will appreciate that numerous modifications may be made thereof without departing from its spirit. For example, while the mask illustrated is intended to be used with a single eye shield, the mask may in fact be provided with two openings to retain shields over both eyes. Furthermore, the shield, while principally designed for use over the eye, may be effectively applied over other parts of the body, in which case other sizes may be more suitable. In fact, children's sizes may also be provided smaller than the examples given when the device is intended for use as an eye shield. Therefore, I do not intend to limit the scope of this invention to the embodiments illustrated and described. Rather, it is intended that the scope of the invention be determined by the appended claims and their equivalents.

What is claimed is:

1. A protective eye shield comprising
    a sealed bag made of a thin, flexible, liquid impervious, transparent material and sized to fit over the eye of a patient and rest upon the surrounding orbital bone structure of the face to form a sealed chamber over the eye, said bag being filled with a liquid; and
    means contacting said bag in unattached relation therewith for holding said bag against the orbital bone structure of the face of a patient in fixed, noncontacting relation with the eyeball for protection of the eyeball by applying pressure to said bag against the orbital bone structure of the face, said holding means including an adjustable strap for surrounding the head of the patient and an opening for permitting viewing of the eye of the patient through said bag;
    said bag being maintained in fixed relation with respect to said holding means and the orbital bone structure only by the external pressure applied thereto by said holding means.

2. A protective eye shield as defined in claim 1 further characterized by
    said bag being made of upper and lower sheets of plastic material approximately one mil in thickness.

3. A protective eye shield as defined in claim 1 further comprising:
    an opening disposed in a wall of said bag; and
    a membrane covering said opening which allows the liquid in the bag to defuse slowly through said membrane to enable liquid in the bag to pass into the sealed chamber over the eye.

4. A protective eye shield as defined in claim 3 further characterized by
    said liquid containing a medicament in solution.

5. A protective eye shield as defined in claim 1 wherein said holding means comprises,
    a mask having an opening smaller than the bag and sized to overlie and engage the periphery of the bag and hold it against the orbital bone structure of the face and form a curvature in the bag within the opening so as to magnify the eye when viewed through the bag.

6. A protective eye shield as defined in claim 4 wherein said holding means comprises,
    a mask having an opening smaller than the bag and sized to overlie and engage the periphery of the bag and engage the periphery of the shield and hold it against the orbital bone structure of the face and form a curvature in the bag within the opening so as to magnify the eye when viewed through the bag.

7. A protective eye shield as defined in claim 1 further characterized by
said strap having a hook and loop closure.

8. A shield as defined in claim 2 further characterized by
said shield being approximately 8×12 cm in plan and 1½ cm in thickness when placed on a flat surface.

9. A protective eye shield as defined in claim 1 further characterized by a self sealing nipple attached to the flexible material through which a needle may be inserted to introduce material into the bag.

* * * * *